US010194698B2

(12) United States Patent
Belcastro et al.

(10) Patent No.: US 10,194,698 B2
(45) **Date of Patent: *Feb. 5, 2019**

(54) INDIRECTLY HEATED CAPILLARY AEROSOLL GENERATOR

(71) Applicant: Philip Morris USA Inc., Richmond, VA (US)

(72) Inventors: Marc D Belcastro, Glen Allen, VA (US); Jeffrey A Swepston, Powhatan, VA (US)

(73) Assignee: Philip Morris USA Inc., Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/475,889

(22) Filed: Mar. 31, 2017

(65) Prior Publication Data

US 2017/0202269 A1 Jul. 20, 2017

Related U.S. Application Data

(63) Continuation of application No. 11/808,496, filed on Jun. 11, 2007, now Pat. No. 9,642,975.

(Continued)

(51) Int. Cl.

| | |
|---|---|
| ***B05B 1/24*** | (2006.01) |
| ***A61M 15/06*** | (2006.01) |

(Continued)

(52) U.S. Cl.

CPC ......... *A24F 47/008* (2013.01); *A61M 11/041* (2013.01); *A61M 11/042* (2014.02);

(Continued)

(58) Field of Classification Search

CPC .. A61M 11/041; A61M 11/042; A61M 15/06; A61M 15/023; A61M 2205/3653;

(Continued)

(56) References Cited

U.S. PATENT DOCUMENTS

| | | | |
|---|---|---|---|
| 3,457,118 A | 7/1969 | Miller | |
| 3,496,668 A | 2/1970 | Slater et al. | |

(Continued)

FOREIGN PATENT DOCUMENTS

| | | |
|---|---|---|
| DE | 19925777 A1 | 1/2000 |
| EP | 1544160 A | 6/2005 |
| JP | 07307139 A | 11/1995 |

OTHER PUBLICATIONS

Sudarsan Srinivasan et al., “Continuous High Pressure Delivery System”, U.S. Appl. No. 11/866,283, filed Oct. 2, 2007.

(Continued)

*Primary Examiner* — Davis Hwu

(74) *Attorney, Agent, or Firm* — Buchanan Ingersoll & Rooney LLC

(57) ABSTRACT

An indirectly heated capillary aerosol generator comprises a capillary tube adapted to form an aerosol when liquid material in the capillary tube is heated to volatilize at least some of the liquid material therein and a thermally conductive material in thermal contact with the capillary tube. The indirectly heated capillary aerosol generator provides substantially even and uniform heating across the heated length of the capillary tube.

15 Claims, 3 Drawing Sheets

Related U.S. Application Data

(60) Provisional application No. 60/812,116, filed on Jun. 9, 2006.

(51) Int. Cl.
*A61M 11/04* (2006.01)
*B05B 17/04* (2006.01)
*A61M 15/02* (2006.01)
*A24F 47/00* (2006.01)

(52) U.S. Cl.
CPC .......... *A61M 15/025* (2014.02); *A61M 15/06* (2013.01); *B05B 1/24* (2013.01); *B05B 17/04* (2013.01); *A61M 2205/3653* (2013.01); *Y10T 29/49083* (2015.01)

(58) Field of Classification Search
CPC ..... B05B 1/24; B05B 17/04; Y10T 29/49083; A61K 9/007; A24F 47/008
USPC .......................................................... 239/338
See application file for complete search history.

(56) References Cited

U.S. PATENT DOCUMENTS

| | | | | |
|---|---|---|---|---|
| 3,731,876 | A | | 5/1973 | Showalter |
| 4,406,943 | A | | 9/1983 | Wilkinson |
| 4,935,624 | A | | 6/1990 | Henion et al. |
| 4,968,885 | A | * | 11/1990 | Willoughby .......... H01J 49/045 250/283 |
| 5,349,186 | A | | 9/1994 | Ikonomou et al. |
| 5,434,765 | A | | 7/1995 | Kelly et al. |
| 5,743,251 | A | | 4/1998 | Howell et al. |
| 6,681,998 | B2 | | 1/2004 | Sharpe et al. |
| 6,682,716 | B2 | * | 1/2004 | Hodges .................. A61K 9/007 128/200.14 |
| 7,128,067 | B2 | | 10/2006 | Byron et al. |
| 9,642,975 | B2 | * | 5/2017 | Belcastro ............. A61M 11/041 |
| 2004/0203175 | A1 | | 10/2004 | Li et al. |

OTHER PUBLICATIONS

International Search Report and Written Opinion dated Dec. 6, 2007 for PCT/IB2007/002713.
International Preliminary Report on Patentability dated Dec. 10, 2008 for PCT/IB2007/002713.

* cited by examiner

INDIRECTLY HEATED CAPILLARY AEROSOLL GENERATOR

CROSS REFERENCE TO RELATED APPLICATIONS

This application is a continuation application of U.S. patent application Ser. No. 11/808,496, filed Jun. 11, 2007, which claims priority under 35 U.S.C. 119 to U.S. Provisional Patent Application No. 60/812,116 filed on Jun. 9, 2006, the entire contents of which are hereby incorporated by reference.

SUMMARY

Provided is an indirectly heated capillary aerosol generator comprising a capillary tube adapted to form an aerosol when liquid material in the capillary tube is heated to volatilize at least some of the liquid material therein and a thermally conductive material in thermal contact with the capillary tube.

Also provided is a method for generating aerosol using an indirectly heated capillary aerosol generator comprising supplying energy to a thermally conductive material of the indirectly heated capillary aerosol generator and supplying liquid material to an inlet of the capillary tube. The thermally conductive material is in thermal contact with a capillary tube of the indirectly heated capillary aerosol generator and the capillary tube is adapted to form an aerosol when liquid material in the capillary tube is heated to volatilize at least some of the liquid material therein. Sufficient energy is supplied to the thermally conductive material such that the thermally conductive material supplies sufficient heat to the liquid material in the capillary tube to volatilize liquid material in the capillary tube and volatilized liquid material is driven out of an outlet of the capillary tube and mixes with ambient air to form aerosol.

Further provided is a method for forming an indirectly heated capillary aerosol generator comprising forming longitudinally extending semicircular grooves along a center axis of two corresponding half cylinders of a thermally conductive material, such that if the two half cylinders were placed together they form a cylindrical shell, and encasing the capillary tube with the two half cylinders, such that the thermally conductive material is in thermal contact with the capillary tube. The grooves are sized to fit closely around the capillary tube and the capillary tube is adapted to form an aerosol when liquid material in the capillary tube is heated to volatilize at least some of the liquid material therein.

DETAILED DESCRIPTION

Figure 1:
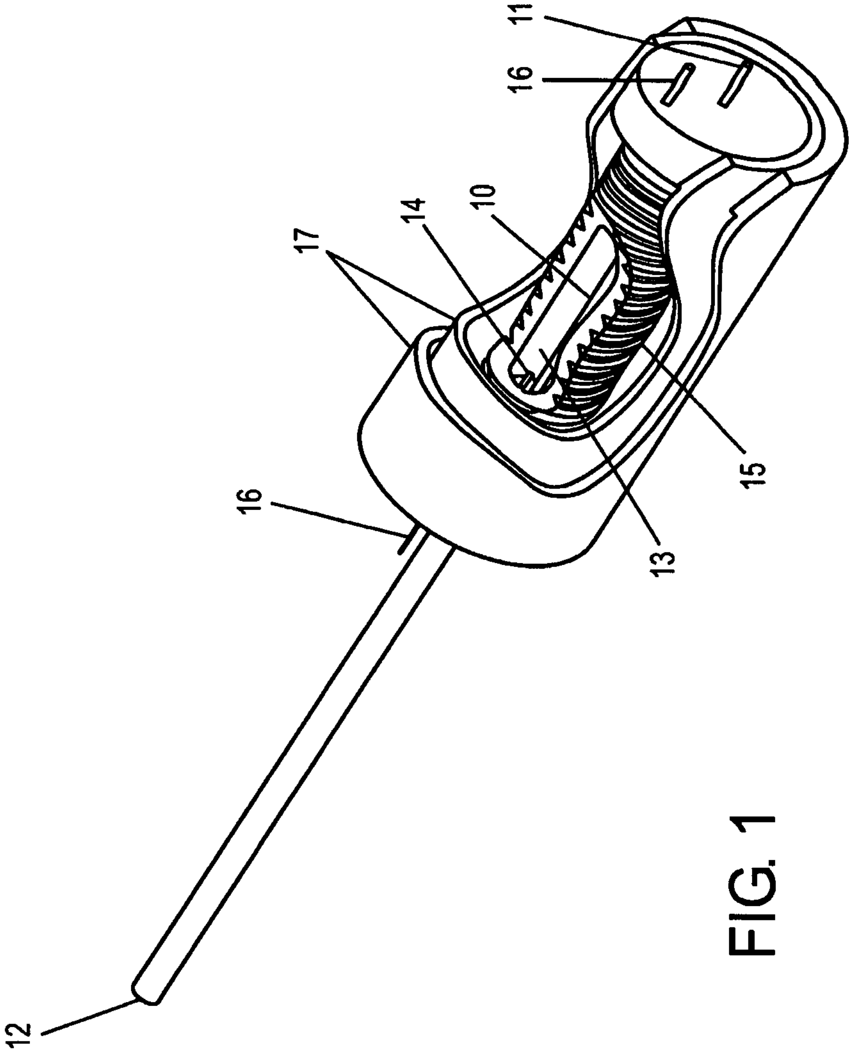
FIG. 1 illustrates an embodiment of an indirectly heated capillary aerosol generator.

Capillary aerosol technology and capillary aerosol generators have been described in U.S. Pat. No. 5,743,251, the contents of which are hereby incorporated by reference in their entirety.

Inhaleable flavored aerosols, for example, tobacco flavored aerosol, which may be used to implement or simulate a smoking experience or other applications, may be generated from a capillary aerosol generator, the length of which can depend on heat requirements dictated by, among other factors, the composition of the aerosol generated. A potential problem associated with directly heated capillary aerosol generators is broad temperature variations inside the capillary tube that may lead to overheating and substandard aerosol formation, resulting in clogging of the capillary tube and/or total failure of a capillary aerosol generator.

A preferred embodiment provides a capillary aerosol generator which includes a capillary tube having an inlet and an outlet. A thermally conductive material is positioned adjacent to the capillary tube, such that the thermally conductive material maximizes heat transfer substantially evenly and uniformly from the thermally conductive material to the capillary tube. The thermally conductive material is preferably wrapped with heating wire and has electrical leads attached to it. The electrical leads are connected to a power source. The power source is selected in view of the characteristics of the components of the capillary aerosol generator.

In operation, electrical leads transfer power from the power source to the heating wire that is wrapped around the thermally conductive material, thereby heating the thermally conductive material. When heated, the thermally conductive material transfers heat to the capillary tube and thus substantially evenly and uniformly heats the capillary tube to a temperature sufficient to volatilize liquid material that is introduced to the heated capillary tube. The liquid material introduced to the heated capillary tube is volatilized and is driven out of the outlet of the capillary tube. The volatilized material mixes with ambient air outside of the capillary tube and forms a condensation aerosol.

The heating wire preferably has an outside diameter of 0.0113 inches, a resistance of 6.6 ohms per foot, and a specific heat of 0.110 BTU/lb-° F. The composition of the heating wire is preferably 71.7% iron, 23% chromium, and 5.3% aluminum. Such a heating wire is available from Kanthal Furnace Products, Bethel, Conn.

The capillary tube preferably has an inside diameter in the range of about 0.05 to 0.53 millimeters, more preferably in the range of about 0.1 to 0.2 millimeters. A particularly preferred inside diameter of the capillary tube is approximately 0.1 millimeter. The capillary tube may be comprised of a metallic or non-metallic tube. For example, the capillary tube may be comprised of stainless steel or glass. Alternatively, the capillary tube may be comprised of, for example, fused silica or aluminum silicate ceramic, or other substantially non-reactive materials capable of withstanding repeated heating cycles and generated pressures and having suitable heat conduction properties may also be used. As the thermally conductive material is in thermal contact with the capillary tube, capillary tubes with low or high electrical resistance may be used. If desired or necessary, an inside wall of the capillary tube may be provided with a coating for reducing the tendency of material to stick to the wall of the capillary tube, which may result in clogging.

Liquid material is preferably introduced into the capillary tube through an inlet of the capillary tube connected to a source of liquid material. The volatilized material is driven out of the capillary tube through the outlet of the capillary tube, i.e., back pressure of liquid from the source of liquid material causes the volatilized liquid to be ejected from the outlet. The back pressure of the liquid is preferably between about 20 to 30 pounds per square inch.

Electrical current passed directly through a conductive capillary tube may provide uneven heating across the length of the capillary tube, with temperature variations inside the capillary tube on the order of about 50 to 100° C. possible. In contrast, an indirectly heated capillary aerosol generator provides substantially even and uniform heating across the heated length of the capillary tube. Because the thermally conductive material of the indirectly heated capillary aerosol generator has a mass that is preferably at least about ten times (e.g., about twenty times, about thirty times, about forty times, about fifty times, about sixty times, etc.) the mass of the capillary tube and the heating wire is preferably equally distributed across the length of the capillary tube, the temperature inside the capillary tube preferably varies by less than about 5° C. Further, by providing electrical energy to the heating wire in a controlled manner, the temperature inside the capillary tube can be accurately maintained.

Since the indirectly heated capillary aerosol generator provides substantially even and uniform heat distribution along the length of the capillary tube, liquid material or volatilized liquid material can be heated to a desired temperate range without overheating the liquid. Overheating may cause substandard aerosol formation and/or result in clogging of the capillary tube and/or total failure of a capillary aerosol generator.

In an indirectly heated capillary aerosol generator, the temperature of the thermally conductive material is heated to and maintained at an operating temperature (i.e., a temperature at which liquid material in the capillary tube is volatilized), which may be in the range of about 250 to 400° C. In an indirectly heated capillary aerosol generator, the flow of liquid material in the capillary tube has limited to minimal impact on the amount of energy the capillary aerosol generator requires to maintain the operating temperature.

The indirectly heated capillary aerosol generator may be fabricated by encasing a capillary tube in a thermally conductive material. The thermally conductive material may take the form of two aluminum half cylinders, in which longitudinally extending semicircular grooves sized to receive the capillary tube are formed. The semicircular grooves run along a center axis of the half cylinders, such that if the half cylinders were placed together they form a cylindrical shell. The grooves are preferably sized to fit closely around the capillary tube. Preferably, the thermally conductive material has a threaded exterior similar to a thread on a typical screw to facilitate attachment of end caps to each end of the mated half cylinders. The aluminum half cylinders are optionally anodized. While anodization makes the electrically conductive parts non-conductive, it does not negatively impact the thermal conductance of the aluminum parts.

Preferably, a high temperature bushing is applied to each end of the capillary aerosol generator to allow for the easy addition of heating wire and electrical leads. Heating wire is preferably wrapped along the entire length of the thermally conductive material. The length of the capillary aerosol generator may be in the range of a few millimeters to hundreds of millimeters (e.g., about 25 to 35 millimeters), depending on the heat requirement dictated by the liquid material makeup and flow rates. However, with the thermally conductive material the capillary passage can be 50 millimeters or longer and still be provided substantially even and uniform heating.

A thermocouple is preferably incorporated into the capillary aerosol generator. Placement of the thermocouple is preferable to ensure accurate temperature monitoring. By utilizing the thermocouple as a feedback device, a closed loop temperature control system can be used to control the temperature of the capillary tube. To complete the capillary aerosol generator package, electrical and liquid material connectors are added.

With reference to FIG. 1, the capillary tube 10 of an indirectly heated capillary aerosol generator has an inlet 12 and outlet 11, as described above. The capillary tube 10 is surrounded by thermally conductive material 13. The temperature of the thermally conductive material 13 may be monitored by use of a thermocouple 14. The thermally conductive material 13 is preferably wrapped with heating wire 15. Electrical leads 16 are preferably attached to the heating wire. The thermally conductive material may be surrounded by insulating sheaths 17.

Figure 2:
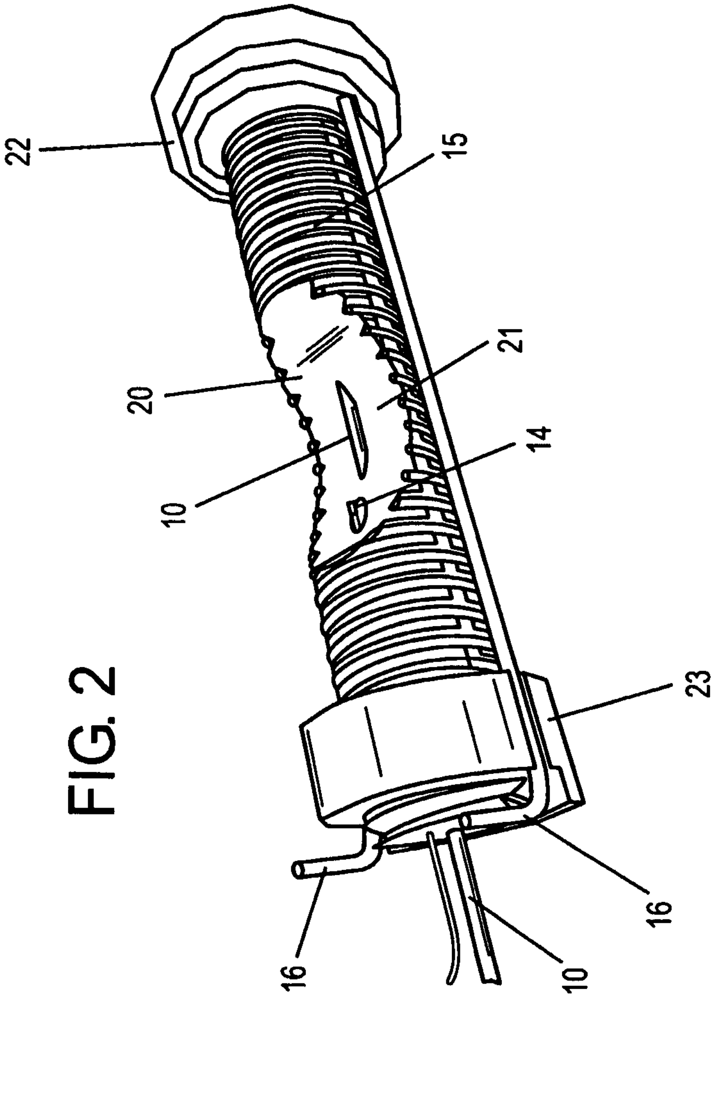
FIG. 2 illustrates another embodiment of an indirectly heated capillary aerosol generator.

With reference to FIG. 2, the capillary tube 10 of an indirectly heated capillary aerosol generator is preferably surrounded by a top half cylinder 20 and bottom half cylinder 21, each of which is comprised of thermally conductive material. The temperature of the thermally conductive material may be monitored by use of a thermocouple 14. The thermally conductive material is preferably wrapped with heating wire 15. Electrical leads 16 are preferably attached to the heating wire. The indirectly heated capillary aerosol generator preferably further includes a front bushing 22, corresponding to the outlet end of the capillary tube, and a rear bushing 23, corresponding to the inlet end of the capillary tube.

Figure 3:
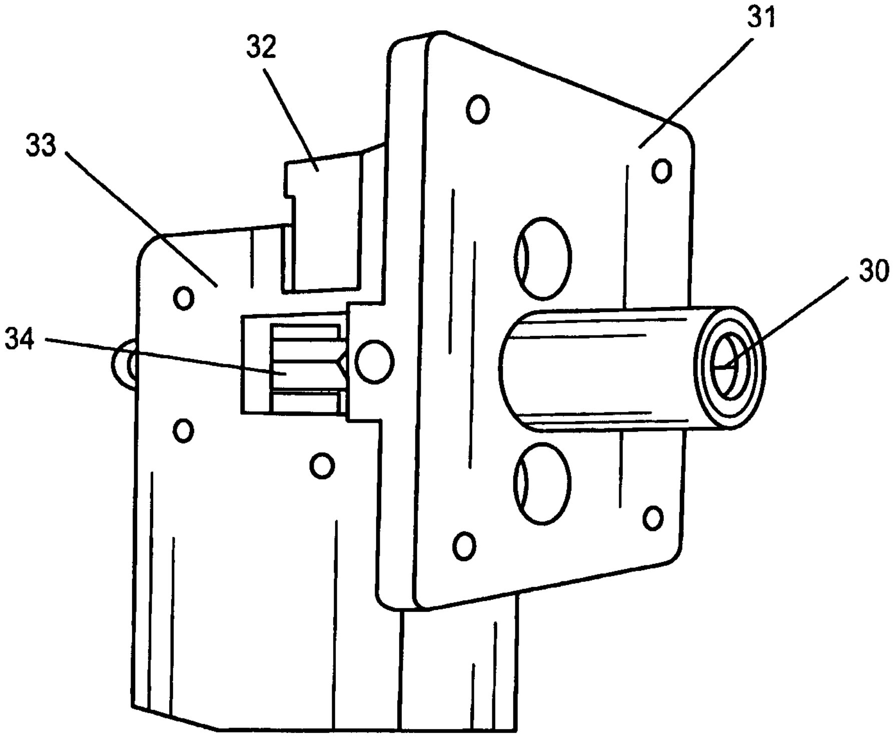
FIG. 3 illustrates an embodiment of an indirectly heated capillary aerosol generator package.

With reference to FIG. 3, an indirectly heated capillary aerosol generator package preferably includes an indirectly heated capillary aerosol generator 30, as described above with reference to FIGS. 1 and 2, a face plate 31, an electrical connector 32, a main body bracket 33, and a liquid material connector 34.

In summary, the thermally conductive material provides uniform heating of a capillary tube around which the thermally conductive material forms a rod (e.g., metallic rod encasing the capillary tube), though the thermally conductive material itself may be heated non-uniformly along the length thereof (e.g., heat may be provided to an outer periphery of the sleeve of thermally conductive material at localized areas, such as through a helically extending resistance heating wire with spacing between turns of the heating wire, as seen in FIG. 2). Thus, the rod of thermally conductive material is thick enough, or has enough mass, to evenly distribute heat from an outer periphery of the rod, through the thermally conductive material, to the capillary tube. However, the rod is not so thin, or without enough mass, such that locations along the capillary tube, and more specifically temperatures inside the capillary tube, experience great variation in temperatures (i.e., temperatures preferably vary by less than about 5° C.) along the heated length of the capillary tube, i.e., the portion of the capillary tube in contact with the surrounding rod of thermally conductive material.

For example, with reference to FIGS. 1 and 2, the rod of thermally conductive material preferably has an outer diameter that is at least three times the outer diameter of the capillary tube (e.g., the outer diameter of the rod can be at least four times, five times, six times, seven times, eight times, nine times, or ten times the diameter of the capillary tube). In particular, for a capillary tube having an outer diameter of about 0.2 millimeters, an outer diameter of the thermally conductive material is preferably at least about 0.6 millimeters (e.g., at least about 0.8, 1.0, 1.2, 1.4, 1.6, 1.8, or 2.0 millimeters). As shown in FIG. 2, the capillary tube and rod arrangement are held together with bushings at each end of the rod and the bushings fit within a tubular housing as shown in FIG. 1. The housing can include the inner tubular member and outer tubular member (i.e., insulating sheaths) shown in FIG. 1 with the outer diameter of the housing being on the order of 3 to 5 mm.

As shown in FIG. 1, the outlet end of the capillary tube may extend beyond one or both ends of the thermally conductive material, which may take the form of a metallic rod, for example, a threaded metallic rod, and the tubular housing (i.e., insulating sheath(s)) of the capillary aerosol generator. As shown in FIG. 2, end caps or bushings attached to, for example, threadedly attached to, opposite ends of the threaded metallic rod, may provide discrete areas upon which inner and outer tubular members of the housing may be positioned. As shown in FIG. 3, the outlet end of the capillary tube may be located in a recess extending into the axial end of the downstream bushing (end cap). Alternatively, the outlet end of the capillary tube can be flush with the end cap or bushing.

The heating wire, which preferably extends along and is in contact with an outer periphery of the thermally conductive material, is operable to heat the thermally conductive material to a temperature sufficient to form an aerosol when liquid material in the capillary tube is heated to volatilize at least some of the liquid material therein. With further reference to FIG. 2, the heating wire can comprise helical heating wire with spacing between turns. An electrical lead may be attached to an upstream end of the helical wire and another electrical lead may be attached to a downstream end of the helical wire. The electrical leads may supply current that is passed through the resistance heating wire. Bushings (end caps) may be located at each end of the capillary aerosol generator, and a downstream electrical lead may extend from bushing to bushing, with a gap between the return portion of the downstream electrical lead and the helical heating wire as shown in FIG. 2. As shown in FIG. 1, a downstream portion of the capillary tube can extend beyond the sleeve of thermally conductive material and an upstream portion of the capillary tube also is not covered by the thermally conductive material. Thus, the thermally conductive material may have a mass that is at least about ten times a mass per unit length of a heated portion of the capillary tube, the heated portion (i.e., portion at which, for example, thermal energy is supplied to the thermally conductive material) of the capillary tube corresponding to a portion of the capillary tube in thermal contact with the thermally conductive material. The heated portion of the capillary tube is located sufficiently close to the outlet of the capillary tube to effect sufficient heating and an aerosolization of the liquid material passing through the capillary tube.

While various embodiments have been described, it is to be understood that variations and modifications may be resorted to as will be apparent to those skilled in the art. Such variations and modifications are to be considered within the purview and scope of the claims appended hereto.

What is claimed is:

1. An indirectly heated capillary aerosol generator comprising:

a capillary tube adapted to form an aerosol when liquid material in the capillary tube is heated to volatilize at least some of the liquid material therein; and a thermally conductive material in thermal contact with the capillary tube, wherein the thermally conductive material is electrically non-conductive and has a mass that is at least about ten times a mass of a portion of the capillary tube in contact with the thermally conductive material.

2. The indirectly heated capillary aerosol generator of claim 1, wherein the capillary tube is metallic.

3. The indirectly heated capillary aerosol generator of claim 1, wherein the capillary tube comprises stainless steel.

4. The indirectly heated capillary aerosol generator of claim 1, wherein the capillary tube is non-metallic.

5. The indirectly heated capillary aerosol generator of claim 1, wherein the capillary tube comprises fused silica.

6. The indirectly heated capillary aerosol generator of claim 1, wherein the thermally conductive material is electrically non-conductive.

7. The indirectly heated capillary aerosol generator of claim 1, wherein the thermally conductive material is comprised of aluminum.

8. The indirectly heated capillary aerosol generator of claim 1, wherein the thermally conductive material is comprised of anodized aluminum.

9. The indirectly heated capillary aerosol generator of claim 1, further comprising a source of liquid adapted to supply liquid material to an inlet of the capillary tube.

10. The indirectly heated capillary aerosol generator of claim 1, further comprising a thermocouple adapted to monitor the temperature of the thermally conductive material.

11. The indirectly heated capillary aerosol generator of claim 1, further comprising a heating wire wrapped around the thermally conductive material.

12. The indirectly heated capillary aerosol generator of claim 11, wherein the heating wire heats the thermally conductive material such that the temperature in the capillary tube varies by less than about 5° C.

13. The indirectly heated capillary aerosol generator of claim 11, wherein the heating wire is adapted to heat the capillary tube to a temperature in the range of about 250° C. to 400° C. to eject volatilized liquid material from an outlet of the capillary tube.

14. The indirectly heated capillary aerosol generator of claim 1, wherein the thermally conductive material comprises a metallic rod and a heating wire extends helically along and in contact with an outer periphery of the metallic rod such that the heating wire is operable to heat localized portions of the metallic rod and the metallic rod transfers heat to the capillary tube to evenly heat the capillary tube to a temperature sufficient to volatilize at least some of the liquid material therein.

15. The indirectly heated capillary aerosol generator of claim 10, further comprising a control system adapted to monitor temperature of the thermally conductive material with the thermocouple and adjust heating of the capillary tube based on the monitored temperature.

* * * * *